United States Patent
Albsmeier et al.

(10) Patent No.: US 9,395,426 B2
(45) Date of Patent: Jul. 19, 2016

(54) ADAPTIVE ENERGY TRANSFER TO A LOCAL COIL SYSTEM

(75) Inventors: Andre Albsmeier, München (DE); Jan Bollenbeck, Eggolsheim (DE); Daniel Evers, Otterfing (DE); Klaus Pistor, Neubiberg (DE); Stefan Schwarzer, Taufkirchen (DE); Markus Vester, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 932 days.

(21) Appl. No.: 13/560,780

(22) Filed: Jul. 27, 2012

(65) Prior Publication Data
US 2013/0200894 A1  Aug. 8, 2013

(30) Foreign Application Priority Data
Jul. 29, 2011  (DE) .......................... 10 2011 080 141

(51) Int. Cl.
| G01R 33/36 | (2006.01) |
| --- | --- |
| A61B 5/055 | (2006.01) |
| G01R 33/28 | (2006.01) |
| G01R 33/3415 | (2006.01) |

(52) U.S. Cl.
CPC ............. G01R 33/36 (2013.01); A61B 5/055 (2013.01); G01R 33/3692 (2013.01); G01R 33/288 (2013.01); G01R 33/3415 (2013.01)

(58) Field of Classification Search
CPC .. G01R 33/36; G01R 33/288; G01R 33/3415; G01R 33/3692; A61B 5/055
See application file for complete search history.

(56) References Cited

U.S. PATENT DOCUMENTS

| 6,233,476 | B1 * | 5/2001 | Strommer et al. ............. 600/424 |
| --- | --- | --- | --- |
| 7,417,433 | B2 * | 8/2008 | Heid et al. ..................... 324/318 |
| 8,073,551 | B2 * | 12/2011 | McCann et al. ............... 607/101 |
| 8,099,059 | B2 * | 1/2012 | Graesslin et al. ............... 455/73 |
| 8,102,177 | B2 * | 1/2012 | McKinnon ..................... 324/318 |
| 8,188,435 | B2 * | 5/2012 | Podhajsky et al. ............ 250/362 |
| 8,294,465 | B2 * | 10/2012 | Gudino et al. ................ 324/318 |
| 8,684,010 | B2 * | 4/2014 | Shachar et al. ............... 128/899 |

FOREIGN PATENT DOCUMENTS

| DE | 10 2010 028 901 A1 | 11/2011 |
| --- | --- | --- |
| WO | WO 2006/067682 A2 | 6/2006 |
| WO | WO 2009/081378 A1 | 7/2009 |

OTHER PUBLICATIONS

German Office Action dated May 14, 2012 for corresponding German Patent Application No. DE 10 2011 080 141.3 with English translation.
A. Oppelt, "Imaging Systems for Medical Diagnostics: Fundamentals, Technical Solutions, Applications for Systems Applying Ionizing Radiation, Nuclear Magnetic Resonance and Ultrasound," pp. 540-541, 2005.

* cited by examiner

Primary Examiner — Dixomara Vargas
(74) Attorney, Agent, or Firm — Lempia Summerfield Katz LLC

(57) ABSTRACT

A method for wireless transfer of energy to a local coil system for a magnetic resonance system is provided. The method includes determining an energy requirement value representing a minimum energy level to be fed to the local coil system, so that the local coil system may carry out a predetermined function over a predetermined time period. Energy is transferred adaptively to the local coil system depending on the energy requirement value.

20 Claims, 2 Drawing Sheets

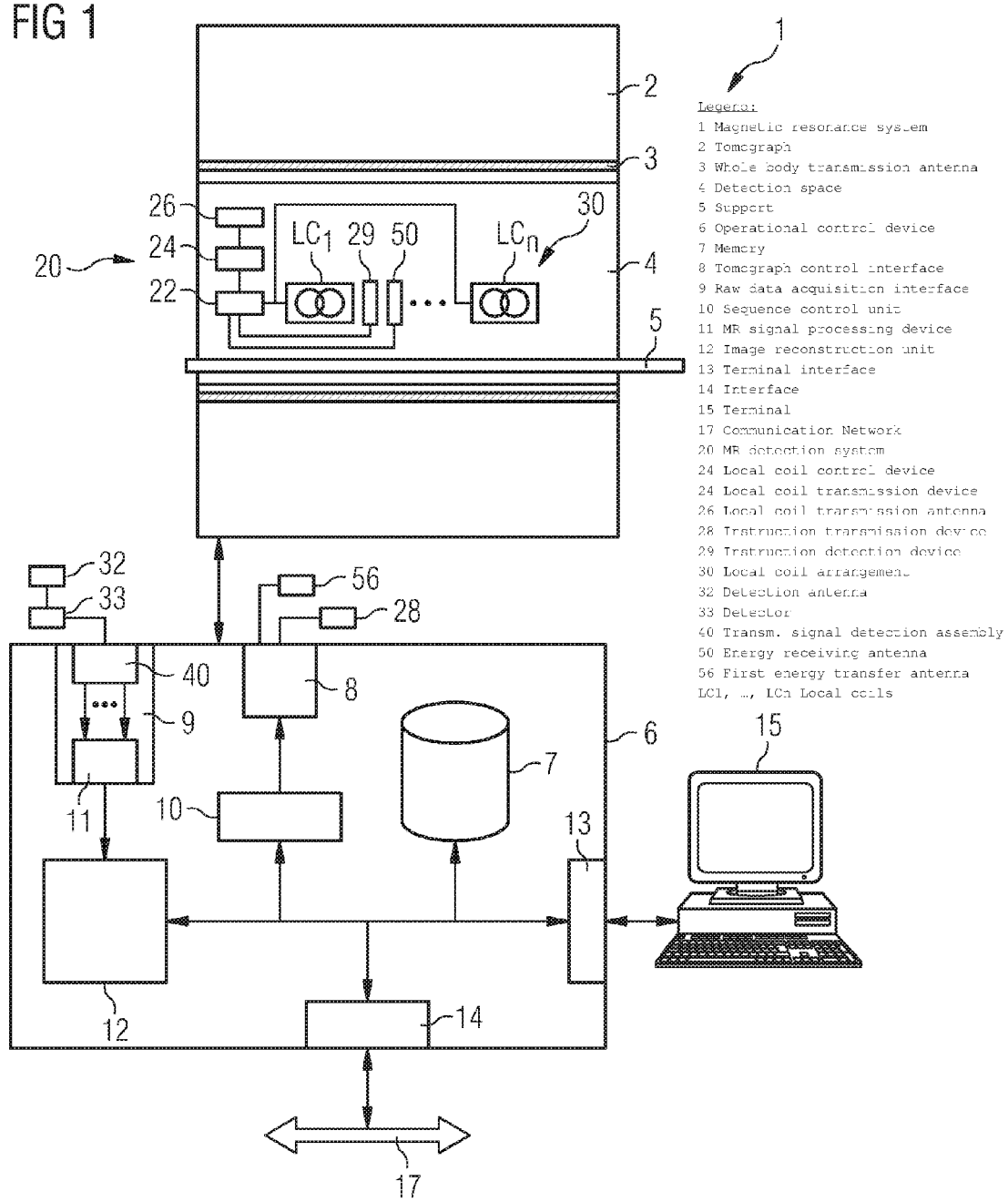

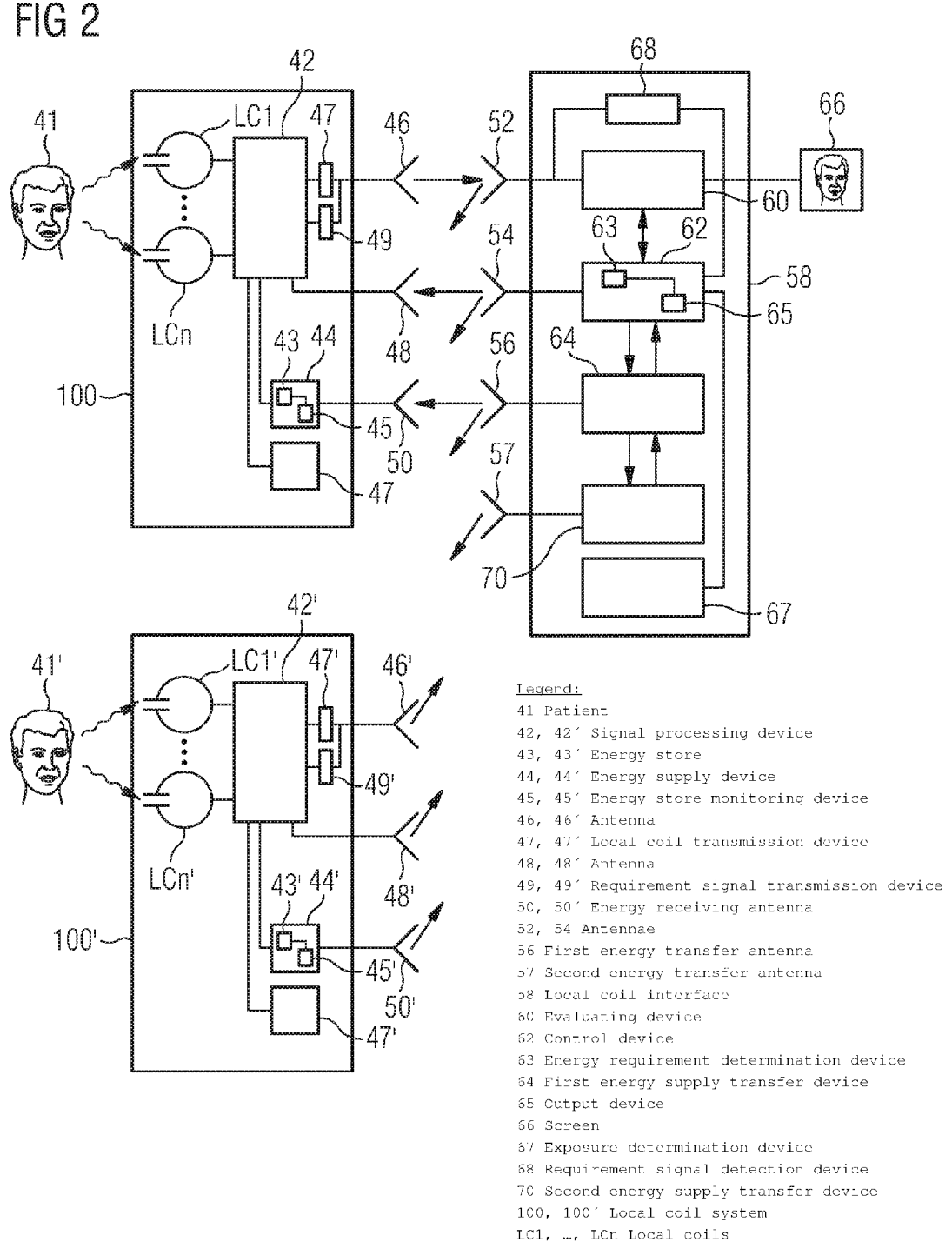

ADAPTIVE ENERGY TRANSFER TO A LOCAL COIL SYSTEM

This application claims the benefit of DE 10 2011 080 141.3, filed on Jul. 29, 2011.

BACKGROUND

The present embodiments relate to a method for the wireless transfer of energy to a local coil system for a magnetic resonance system.

Imaging with a magnetic resonance tomography system is carried out essentially in three steps. Initially, a strong, stable homogeneous magnetic field, and thus a stable orientation of the nuclear spin of the protons, is generated in a region under examination (e.g., a region of the body of a patient). This stable orientation is then altered by feeding in high frequency electromagnetic energy (e.g., magnetic resonance excitation signals or MR excitation signals). This may be achieved with a whole-body antenna arranged fixed in the magnetic resonance tomograph (e.g., a "birdcage" antenna) that surrounds the examination space, in which the patient is situated during the examination. The energetic stimulation is ended, and the magnetic resonance signals (e.g., magnetic resonance detection signals or MR detection signals) arising in the examination region on relaxation of the nuclear spin are detected with the aid of suitable detection antennae (e.g., detection coils) in order to be able to draw conclusions about the material or tissue in the examination region. On excitation and/or acquisition of the MR detection signals, rapidly switched magnetic field gradient pulses are transmitted with a gradient coil system for position encoding. A magnetic resonance tomography system therefore includes a plurality of cooperating components, each of which uses of modern and complex technologies.

In a magnetic resonance examination, "local coils" may be used to receive the MR detection signals, so as to achieve the best possible signal-to-noise ratio (SNR). The local coils include detection antenna assemblies that have at least one detection antenna element (e.g., a plurality of detection antenna elements) in the form of, for example, conductor loops that are mounted closely on, under or at the patient. The local coils may be arranged in a "local coil mat" that is laid over or under the body of the patient. In many examinations, a plurality of local coils of this type is arranged at the patient to cover whole regions of the body of the patient. The MR detection signals received may be pre-amplified in the local coil and are conducted out of the central region of the magnetic resonance system via cables and fed to a screened receiver of an MR signal processing device. In the device, the received data are then further processed.

The structure and function of magnetic resonance systems is known and is described, for example, in Imaging Systems for Medical Diagnostics, edited by Arnulf Oppelt, Publicis Corporate Publishing, ISBN 3-89578-226-2, and further detailed discussion is unnecessary.

Due to the MR excitation signals for stimulation of nuclear spin, the patient is subjected to a physiological high frequency exposure. During imaging, it is to be provided that the patient is not harmed by such physiological high frequency exposure. In the development and establishment of magnetic resonance tomography systems, therefore, limit values that define the maximum physiological high frequency irradiation of a human body or the high frequency exposure of the human body are standardized to provide patient safety. A typical limit value for this is the maximum admissible specific absorption rate (SAR) value For example, it is required for the "whole body SAR" that the power absorbed by the patient averaged over a time window of 6 minutes is to not exceed a value of 4 W/kg with physiological monitoring. In magnetic resonance systems, measuring devices, with which the high frequency power may be measured, are provided. For this purpose, directional couplers may be used in the feed lines from a high frequency amplifier to the antenna system in order to transmit the MR excitation signals.

The signals from the local coils are transmitted from the local coils by cables to an evaluating device of the magnetic resonance system. The cables are undesirable because the cables cannot easily be fed from the patient support to the evaluating device, since the patient support is moved with the patient, and the local coil mat and consequently the cables hang loosely. The cables are therefore often found to be a nuisance.

In order that no cables are connected to the local coil mat, the received MR detection signals are transmitted to the MR signal processing device and power supply to the local coils are provided wirelessly. In order to transfer energy to the local coil mat, for example, inductive methods may be used. The inductive transfer of energy to the local coil produces additional physiological high frequency exposure of the human body. Consequently, the physiological high frequency exposure due to the actual imaging is kept low if energy is also transferred wirelessly to the local coil system, in order that the maximum permissible physiological high frequency exposure of the patient is not exceeded by the imaging and the wireless energy supply.

SUMMARY AND DESCRIPTION

The present embodiments may obviate one or more of the drawbacks or limitations in the related art. For example, a physiological high frequency exposure due to the wireless transfer of energy to a local coil system is reduced.

In one embodiment of a method for the wireless transfer of energy to a local coil system for a magnetic resonance system, an energy requirement value representing a minimum energy level to be fed to the local coil system is determined in each case, so that the local coil system may carry out a predetermined function over a predetermined time period. Depending on the energy requirement value, an adaptive transfer of a quantity of energy to the local coil system is carried out.

The expression "adaptive transfer of a quantity of energy" may be that a current energy requirement is determined repeatedly, for example, at regular time points and/or before each transfer of energy to the local coil system, such that the quantity of energy to be transferred is adapted to the actual requirement or the requirement expected for the predetermined time period. It is provided that energy is only transferred wirelessly to the local coil system when the local coil system needs a transfer of energy. The physiological high frequency exposure of a patient may therefore be reduced to a degree necessary for the energy supply. The largest possible proportion of the permissible physiological high frequency exposure may be available for the actual imaging. This favors the quality of the recordings.

In one embodiment, a local coil energy supply arrangement for a local coil system includes an energy requirement determination device that is configured to determine an energy requirement representing a minimum energy level to be fed to the local coil system, so that the local coil system may perform a predetermined function over a predetermined time period. The local coil energy supply arrangement also has an energy supply transfer device for wireless supply of a local coil system with energy. The energy output by the energy supply transfer device depends on the energy requirement value (e.g., the energy supply transfer device is configured so as to control the energy transfer adaptively).

As described in greater detail below, the energy requirement determination device may be arranged in a local coil system or in a control device arranged separately from the local coil system (e.g., in a central control unit of the magnetic resonance tomograph), or the components of the energy requirement determination device may be distributed over the local coil system and other control devices of the magnetic resonance tomograph.

In another embodiment, a local coil system includes, apart from a number of local coils or antenna elements that are configured in order to receive magnetic resonance detection signals, a local coil transmission device and an energy receiving device. The energy receiving device is configured to receive energy wirelessly, for example, in the form of electromagnetic waves. The local coil transmission device is configured to transmit magnetic resonance transmission signals based on the magnetic resonance detection signals. The magnetic resonance transmission signals are, for example, pre-amplified and pre-processed magnetic resonance detection signals (e.g., processed for transmission to a detector of the magnetic resonance system). Thus, the local coil system may be wirelessly supplied with energy, and the magnetic resonance detection signals received are transmitted wirelessly as magnetic resonance detection signals to an MR signal processing device. The local coil system also includes an energy requirement determination device configured to communicate whether the local coil system requires an energy transfer, and a requirement transmission device that is configured to transmit an energy requirement indicating that the local coil system requires a supply of energy.

In one embodiment, a magnetic resonance system includes a local coil energy supply arrangement, as described above, and/or a local coil system, as described above.

The description of one category may be further developed similarly to another category.

In the context of the method according to the present embodiments, a value for a first physiological high frequency exposure, to which a patient is subjected due to the energy transferred from an energy transfer device to an energy receiving device of the local coil system, may be determined. A second physiological high frequency exposure value being the maximum that may be caused through imaging with magnetic resonance excitation signals may also be determined, in order that the maximum permissible physiological high frequency exposure due to the first physiological high frequency exposure value and the second physiological high frequency exposure value is not exceeded. For this purpose, for example, the local coil energy supply arrangement and/or the local coil system may include a suitable exposure determination unit that is configured to determine the first physiological high frequency exposure value and/or the second physiological high frequency exposure value. The second physiological high frequency exposure value may also be determined, for example, as the difference between a permissible limit value and the first physiological high frequency exposure value.

If the first and second high frequency exposure values are known, the ratio between the first and second physiological high frequency exposure values may be optimized. The optimization may take place such that the smallest possible proportion of the physiological high frequency exposure is incurred during the wireless energy transfer. The acts of determining a first physiological high frequency exposure value, of determining a second physiological high frequency exposure value, and of optimizing the ratio between the first physiological high frequency exposure value and the second physiological high frequency exposure value may be repeated, for example, in regular intervals and/or before an energy transfer, and the ratio may be adaptively changed. Since the physiological high frequency exposure also contains a time component (e.g., the measure involves a distribution of the high frequency energy over a particular time interval), and chronological peak values are to be avoided, how high the physiological high frequency exposure is expected to be and in which time periods, due to the actual imaging, may be estimated. Thus, optimizing of the energy transfer to the local coil system may also be planned accordingly on the basis of the energy requirement value, so that relatively large energy values are transferred and stored in a local energy store of the local coil system, for example, precisely when no physiological high frequency exposure takes place due to the imaging (e.g., over a particular time period when, temporarily, no MR excitation signals are transmitted).

The predetermined functions, for which the local coil system requires energy, may involve reception of MR detection signals, pre-processing the MR detection signals and/or transmission of the magnetic resonance transmission signals based on the magnetic resonance detection signals.

Accordingly, a transfer energy requirement value that indicates the energy required by the local coil system in order to transmit magnetic resonance transmission signals with the local coil transmission device to the evaluating device may be determined as the energy requirement value. Alternatively or additionally, a pre-processing energy requirement value that indicates the energy required by the local coil system to evaluate and/or to prepare the magnetic resonance detection signals may be determined. Only as much energy as is needed to carry out the currently required functions of the local coil system is transferred to the local coil system. For example, the local coil system may function such that initially only magnetic resonance detection signals are received, pre-processed and may be locally digitized and stored in a memory in the local coil system. The local coil system may also function such that the digitized magnetic resonance detection signals are only later transferred as magnetic resonance transmission signals when the required energy is available again. In this way, the physiological high frequency exposure of the patient through the wireless energy transfer may be minimized.

In the process of determining the energy requirement value, information about the pulse sequences to be emitted (e.g., the magnetic resonance excitation signals and/or gradient pulses that may, for example, be accepted by the magnetic resonance sequence control is to be taken into account). If the pulse sequences (e.g., the type, energy, repetition of the magnetic excitation signals) are known, the detection activity may be estimated in advance. Thus, at what time point or time points which quantity of energy is to be transferred may be calculated so that the local coil system may receive the magnetic resonance detection signals, further process the signals to magnetic resonance transmission signals and may transmit the magnetic resonance transmission signals to a detector. Before the actual imaging, at which time points energy is to be transferred to the local coil system may be calculated. This facilitates the performance of planning automatically before the imaging, so that the ratio of the first physiological high frequency exposure value to the second physiological high frequency exposure value may be optimized, as described above.

Patient-specific data may be taken into account in order to determine the energy requirement value. For example, the mass of the patient, to which the antennae are exposed, may be taken into account.

The manner of the investigation for determining the energy requirement value may also be taken into account. Which body parts are subjected to imaging may, for example, be taken into account. The spacing intervals and the resolution, at which the imaging is to be carried out, may also be considered. The type and number of the local coils used may also be taken into account.

The current power emitted and returning to/from an antenna for transmitting magnetic resonance excitation signals and/or the power emitted and returning to/from an energy supply antenna may be measured and taken into account in the determination of the energy requirement value. By this, the energy actually emitted by the antennae may be calculated very precisely, and the energy requirement value may be better estimated.

The energy stored in an energy store of the local coil system may also be taken into account in the determination of the energy requirement value. For this purpose, the local coil system may have a suitable energy store that may be charged up before use of the local coil system, so that during reception of the magnetic resonance detection signals and the transfer of the magnetic resonance transmission signals, the patient is subjected to a minimum of physiological high frequency exposure.

If the energy store contains so little energy that reliable operation is currently or in a predetermined time-frame no longer possible, a signal that indicates that the energy store of the local coil system is to be recharged is output. The physiological high frequency exposure of the patient may be further reduced.

For this purpose, the local coil supply arrangement may include an energy store monitoring device that is configured to monitor an energy store and to generate an energy requirement signal that represents the energy status of the energy store and a requirement signal detection device that is configured to detect the energy requirement signal. The energy store monitoring device may thus inform the local coil supply arrangement that the local coil system needs extra energy. In the simplest case, the energy store monitoring device may be arranged locally in the local coil system and monitor the energy store state (e.g., charge state) directly. The energy requirement signal may output the current charge state quantitatively in each case, so that the value may be used in the calculation of the current energy requirement value. The energy requirement signal may also indicate that an energy requirement currently exists, for example, if the charge state has reached or undershot a predetermined limit value.

An energy store monitoring device of this type may be used both when no device that predictively estimates, for example, before the imaging, what energy requirement the local coil system will have over a predetermined time frame is present, and also in addition to such a device. When the device is present, the energy store monitoring device may be used to offer an additional redundancy (e.g., to verify the calculations and/or in order to update the calculations of the energy requirement value more simply and reliably and thus better to provide that the energy store of the local coil system always has a sufficient charge). The energy store monitoring device may accordingly be configured as part of the energy requirement determination device or, in the simplest case, may be the device.

In one embodiment of the method, an energy supply transfer device may be switched off during a time when no magnetic resonance signals may be received. Therefore, during a predetermined time period, no energy is transferred to at least one local coil system that, for example, does not have to receive any magnetic resonance signals and therefore also does not have to process any such signals or transmit corresponding magnetic resonance transmission signals during the predetermined time period. The physiological high frequency exposure of a patient is thus further reduced.

The expression "energy supply transfer device" is to be interpreted broadly in that the energy supply transfer device may be, for example, an antenna and/or a transmission circuit (e.g., an amplifier).

In one embodiment, a spatially inhomogeneous energy distribution may be deliberately created at least temporarily for energy supply to a local coil system. For this purpose, for example, a first energy supply transfer device that emits power in the direction of a first local region of the patient may be switched off or operated at a reduced level, and a second energy supply transfer device that emits power in the direction of a second local region of the patient may be switched on or operated at an intensified level. For example, a first antenna may be uncoupled from an amplifier and coupled instead to another amplifier for the transfer of energy. This spatially inhomogeneous energy distribution for energy supply to the local coil system may be controlled such that the current spatial distribution of the physiological high frequency exposure due to the imaging and/or the spatial arrangement of various local coil systems at the patient and the current activity and energy requirement thereof are taken into account. For example, a local region of the patient being exposed with energy may be prevented if the local coil systems do not have to receive magnetic resonance signals and do not require energy in the region. In this way, the physiological high frequency exposure of the patient may be further reduced.

BRIEF DESCRIPTION OF THE DRAWINGS

FIG. 1 is a simplified block circuit diagram of an exemplary embodiment of a magnetic resonance system; and FIG. 2 is a simplified block circuit diagram to illustrate the energy transfer and the signal transmission between a local coil system and further components of a magnetic resonance system according to one embodiment.

DETAILED DESCRIPTION OF THE DRAWINGS

FIG. 1 shows a block circuit diagram of one embodiment of a magnetic resonance system 1. The core of the magnetic resonance system 1 is a commercially available tomograph 2 (e.g., a scanner 2), in which a patient (not shown) is positioned on a support 5 in a cylindrical detection space 4. Arranged within the tomograph 2 is a whole-body transmitting antenna arrangement 3 (e.g., a birdcage antenna) for transmitting magnetic resonance excitation signals.

In the exemplary embodiment according to FIG. 1, an MR detection system 20 for detecting the MR detection signals includes a local coil system or a local coil arrangement 30, for example, in the form of a local coil mat with a number of local coils $LC_1, \ldots, LC_n$ and a transmission signal detection assembly 40. As FIG. 1 shows, the local coil arrangement 30 is arranged in the detection space 4 of the tomograph 2 of the magnetic resonance system 1. The transmission signal detection assembly 40 is realized as part of a raw data acquisition interface 9 in an operational control device 6 of the magnetic resonance system 1. The local coil arrangement 30 is connected, as described below, via a wireless interface to the transmission signal detection assembly 40.

A part of the operational control device 6 and/or the raw data acquisition interface 9 is an MR signal processing device 11. The system is scalable to any desired extent (e.g., with suitable design of the MR detection system 20, any desired number of physical inputs from the MR signal processing device 11 may be operated).

The tomograph 2 is also controlled by the operational control device 6. A terminal 15 (or an operating console), using which an operator may operate the operational control device 6 and thereby the tomograph 2 is connected to the operational control device 6 via a terminal interface 13. The operational control device 6 is also connected to the tomograph 2 via a tomograph control interface 8. Using the tomograph control interface 8, suitable control commands are output to the tomograph 2 via a sequence control unit 10 based on scan protocols, so that the desired pulse sequences (e.g., the high frequency pulses and the gradient pulses for the gradient coils (not shown)) are emitted to generate the desired magnetic fields.

The operational control device 6 also includes a memory 7, in which, for example, generated image data may be stored and measuring protocols may be deposited.

A further interface 14 serves to connect to a communications network 17 that is linked, for example, to an image information system (e.g., picture archiving and communication system (PACS)) or offers connection possibilities for external data stores.

The raw data are acquired via the raw data acquisition interface 9, which, for example, includes the transmission signal detection assembly 40 (e.g., the received MR detection signals are read out). In the MR signal processing device 11, the received signals are processed and fed to an image reconstruction unit 12 that generates the desired magnetic resonance image data therefrom in the conventional manner. The data may be stored, for example, in the memory 7 or at least partially output at the terminal 15 or transferred via the communications network 17 to other components (e.g., evaluating stations or mass storage units).

Both the operational control device 6 and the terminal 15 may also be an integral component of the tomograph 2. The overall magnetic resonance system 1 also has all or some of the usual further components and features of such a system, which, for the sake of clarity, are not shown in FIG. 1.

Since the local coil arrangement 30 is to be connected wirelessly to the operational control device 6, an instruction transmission device 28 is also connected to the tomograph control interface 8 that transfers the instructions or control signals wirelessly to the local coil arrangement 30.

A first energy transfer antenna 56 that transfers energy wirelessly to an energy receiving antenna 50 of the local coil arrangement 30 is also connected to the tomograph control interface 8 in order to supply the local coil arrangement with energy. The energy received may be passed on, for example, to the local coil control device 22.

The local coil arrangement 30 with the local coils $LC_1, \ldots, LC_n$ also includes an instruction receiving device 29 that receives the wirelessly transmitted instructions, as described in detail below. The instructions are, for example, also passed on to a local coil control device 22. The local coil control device 22 supplies the local coils $LC_1, \ldots, LC_n$ with energy and controls the coils. MR detection signals detected by the local coils are passed by the local coil control device 22 in processed form (e.g., in digitized form), as MR transfer signals, to a local coil transmission device 24, from where the signals are transmitted via a local coil transmission antenna 26 to a detection antenna 32 of the magnetic resonance system 1. The MR transmission signals received from the detection antenna 32 are evaluated by a detector 33 and fed to the transmission signal detection assembly 40.

FIG. 2 shows a schematic representation of the signal flow between different parts of a first local coil system 100 and further components of the magnetic resonance system that may be arranged, for example, in a local coil interface 58 of the operational control device 6. Not all these components have to be grouped together in a common local coil interface 58, but may be distributed over various other system parts of the magnetic resonance system.

A plurality of local coils $LC_1, \ldots, LC_n$ receive MR detection signals that are emitted by atomic nuclei within a patient 41. The local coils $LC_1, \ldots, LC_n$ are connected to a signal processing device 42 and a local coil transmission device 47 that processes the MR detection signals and emits corresponding MR transmission signals via an antenna 46 to the local coil interface 58 of the magnetic resonance system. The signal processing device 42 receives clock signals and control instructions via an antenna 48. Using the energy receiving antenna 50, energy is fed to the local coil system 100 and, for example, to the signal processing device 42. The energy is rectified and buffered in a local coil system-side energy supply device 44. The energy receiving antenna 50 and the energy supply device 44 together constitute a local coil system-side energy receiving device 44, 50.

The magnetic resonance system receives, using an antenna 52, the MR transmission signals that represent the MR detection signals. The MR transmission signals are processed in an evaluating device 60 (schematically represents an MR signal processing device and an image reconstruction unit in FIG. 1). The evaluating device 60, for example, displays the signals on a screen 66. The evaluating device 60 is coupled to a control device 62. The control device 62 transmits clock signals and instructions via an antenna 54 to the local coil system 100. The control device 62 is also connected to a first energy supply transfer device 64 that transfers energy via a first energy transfer antenna 56 to the first local coil system 100. The first energy supply transfer device 64 and the first energy transfer antenna 56 together constitute a first energy transfer device 56, 64. The local coil interface 58 of the magnetic resonance system includes a second energy supply transfer device 70 that is connected to a second energy transfer antenna 57. The second energy transfer antenna 57 transfers energy in the direction toward a second local coil system 100' that is arranged spaced apart from the local coil system 100. The second energy supply transfer device 70 and the second energy transfer antenna 57 together constitute a first energy transfer device 57, 70. The second local coil system 100' is constructed identically to the first local coil system 100 and includes the same components. The components of the second local coil system 100', which are identical to the first local coil system 100, are identified with an apostrophe after the reference sign and are not described again.

The energy supply device 44 of the first local coil system 100 includes an energy store 43. The energy store 43 is monitored by an energy store monitoring device 45. The energy store monitoring device 45 emits a signal that indicates that the energy store needs a supply of charge when a charge in the energy store 43 falls below a first threshold value. The signal generated by the energy store monitoring device 45 is transmitted by a requirement signal transmission device 49 via the antenna 46 to the magnetic resonance system. The requirement signal may be generated, as shown in FIG. 1, by an on-board transmitting unit 49. The signal may also be included in the digital data stream of the MR signals in the form of additional control words and transmitted by the local coil transmission device 47. This procedure prevents the charge in the energy store 43 falling below the first threshold value and provides that there is sufficient charge in the energy store 43 to enable reliable operation of the local coil system 100 over a predetermined time period. At the same time, this adaptive transfer of energy to the local coil systems 100, 100' provides that a patient is not subjected to any unnecessary physiological high frequency exposure.

A requirement signal detection device 68 detects the signal generated by the energy store monitoring device 45 and conducts the signal to the control device 62. The control device 62 includes an output device 65 that outputs a signal to the first energy supply transfer device 64 or to the second energy supply transfer device 70. The signal outputted by the control device 62 indicates that the first local coil system 100 or the second local coil system 100' requires energy input. Consequently, energy is transferred via the first energy supply transfer device 64 and the first energy transfer antenna 56 to the first local coil system and/or via the second energy supply transfer device 70 and the second energy transfer antenna 57 to the second local coil system 100'.

The magnetic resonance system also includes, for example, an energy requirement determination device 63. The energy requirement determination device 63 may determine, as described below in more detail, whether and to what extent the first local coil system 100 and/or the second local coil system 100' require a supply of energy. If the first local coil system 100 requires a supply of energy, the output device 65 outputs a signal to the first energy supply transfer device 64. The signal outputted by the output device 65 transfers energy via the first energy transfer antenna 56 to the energy receiving antenna 50 of the first local coil system 100. If the second local coil system 100' requires a supply of energy, the output device 65 issues a signal to the second energy supply transfer device 70, where the second energy supply transfer device 70 transfers energy wirelessly via the second energy transfer antenna 57 to the energy receiving antenna 50'.

The energy requirement determination device 63 may determine or estimate, before the actual imaging and before detection of the magnetic resonance signals and/or during imaging, the energy needed by the local coil systems 100 and 100' in order to carry out a predetermined function over a predetermined time period. A variety of procedures and any input parameters to be taken into account were described above. The energy requirement determination device 63 may, for example, determine a transfer energy requirement value that indicates the energy required by the local coil system 100, 100' in order to transmit magnetic resonance transmission signals based on the magnetic resonance detection signals with the local coil transmission device 47 to the magnetic resonance system. The energy requirement determination device 63 may also determine a pre-processing energy requirement that represents the energy required by the local coil system 100, 100' for evaluating and/or preparing the MR detection signals.

The energy requirement value may therefore be determined, for example, in that the energy store monitoring device 45 determines that the energy store 43 of the local coil system 100 does not have sufficient charge to supply the local coil system 100 with energy over a predetermined time period, so as to be able to carry out a predetermined function. However, the energy store monitoring device 45 may also be used as a type of redundancy or control entity in case the energy requirement determination device 63 has not determined the energy requirement correctly, or the energy requirement changes for unforeseeable reasons. Thus, it may be more easily ascertained that the energy store 43 of the local coil system 100 has a sufficient charge in order to carry out a predetermined function over a predetermined period. The predetermined function includes, for example, the detection of magnetic resonance detection signals, as described above, the pre-processing of the magnetic resonance detection signals and/or the transmission of the magnetic resonance transmission signals based on the magnetic resonance detection signals to the magnetic resonance system.

The local coil interface 58 of the magnetic resonance system also includes an exposure determination device 67 that is coupled to the requirement signal detection device 68 and the energy requirement determination device 63. The exposure determination device 67 may determine the expected physiological high frequency exposure of the patient before the actual imaging, as described below in greater detail.

For this purpose, the exposure determination device 67 may determine a first physiological high frequency exposure value, to which the patient is subjected on the basis of the energy emitted by the energy transfer device, 56, 57, 64, 70 to the energy receiving device 44, 50, 44', 50' of the local coil system. The exposure determination device 67 may also determine a second physiological high frequency exposure value that is a maximum that may be caused by imaging with magnetic resonance excitation signals, in order that a maximum permissible physiological high frequency exposure due to the first physiological high frequency exposure value and the second physiological high frequency exposure value for a patient is not exceeded. This may be achieved by finding the difference between the permissible limit values and the second physiological high frequency exposure value.

A permissible sliding mean value for high frequency dissipation in tissue over six minutes is, for example, 2 W/kg or 4 W/kg during physiological monitoring. Only 3.2 W/kg is permissible in the head of a patient. The exposure determination device may calculate the physiological high frequency exposure of a patient (SAR) permitted in the context of imaging, as follows. If an input power rating of the first or second energy supply transfer device in an example case is 300 W, then an estimated 10 W is dissipated in the body of a patient. From this, the maximum permissible physiological high frequency exposure (SAR) of a patient during imaging is found to be 320 W (80 kg*4 W/kg) if physiological monitoring is present. The proportion contributed to the physiological high frequency exposure by the wireless energy transfer is therefore 3.1% (10 W/320 W).

The energy requirement determination device 63 and/or the exposure determination device 67 may therefore be configured such that the devices optimize the ratio between the first physiological high frequency exposure value and the second physiological high frequency exposure value. For example, the ratio may be optimized such that the highest possible proportion of the permitted high frequency exposure is attributable to the imaging, and the lowest possible proportion of the physiological high frequency exposure is caused by the wireless energy supply.

In the exemplary embodiment described, the control device 62 may instruct the first energy supply device 64 during a predetermined time period, during which no magnetic resonance signals are to be detected by the first local coil 100, not to transfer any energy wirelessly via the first energy transfer antenna 56. Similarly, the control device 62 may instruct the second energy supply transfer device 57, 70 not to transfer any energy wirelessly via the second energy transmission antenna to the second local coil system 100' during a time period, in which no magnetic resonance signals are to be detected by the second local coil system 100'. For this purpose, the control device 62 may switch off an energy supply transfer device 64, 70 that emits a power output in the direction of a first local region of the patient while another energy transfer device 56, 64, 57, 70 that emits power in the direction of a second local region of a patient is switched on. Alternatively, the energy transfer antennae 56, 57 may be switched in or decoupled in a suitable manner.

Depending on spatial and temporal criteria, only the local coil systems 100, 100' that actually need energy for imaging are supplied with energy. In accordance with the energy requirement of the spatially distributed local coil systems 100, 100', a corresponding spatially inhomogeneous energy field, from which the local coil systems 100, 100' draw the energy needed, may be created.

According to the present embodiments, the transmission power used for energy transfer is adjusted adaptively to be large enough so that the operation of the local coils is just provided. In this way, the proportion of the physiological high frequency exposure (SAR) resulting from the energy transfer is minimized, and the largest possible proportion of the permissible physiological high frequency exposure remains for the magnetic resonance excitation signal or magnetic resonance transmission signal used for imaging.

At the start of the examination, the minimum necessary transmission power, at which the energy supply to the local coil systems is provided, may be determined. For this purpose, the power received by the local coil system may be taken into account directly. In addition, examination data known in advance (e.g., the mass of the patient, the type of examination, the use of local coils) may be taken into account to optimize the transmission power. From the minimum value of the transmission power of the energy supply determined therefrom, the proportion in the total physiological high frequency exposure is found. From this, the maximum possible proportion of the physiological high frequency exposure attributable to the magnetic resonance transmission signal for the imaging may be calculated.

The methods and devices described above are exemplary embodiments, and the underlying principle may be varied within broad limits by a person skilled in the art without departing from the scope of the invention. The use of the indefinite article "a" or "an" does not preclude the relevant feature being present more than once. The expression "unit" also does not preclude an item consisting of a plurality of components, which may also be spatially distributed.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for wireless transfer of energy to a local coil system for a magnetic resonance system, the method comprising:
   repeatedly determining, using an energy requirement determination device, an energy requirement value representing a minimum energy level to be fed to the local coil system for the local coil system to carry out a predetermined function over a predetermined time period;
   adaptively transferring, by an energy transfer device, a quantity of energy wirelessly to the local coil system depending on the respective determined energy requirement value; and
   carrying out, by the local coil system, each predetermined function over each predetermined time period using the respective transferred quantity of energy.

2. The method as claimed in claim 1, further comprising:
   determining a first physiological high frequency exposure value, to which a patient is subjected due to the energy transferred from an energy transfer device to an energy receiving device of the local coil system; and
   determining a second physiological high frequency exposure value being a maximum caused through imaging with magnetic resonance excitation signals, in order that a maximum permissible physiological high frequency exposure due to the first physiological high frequency exposure value and the second physiological high frequency exposure values is not exceeded for the patient.

3. The method as claimed in claim 2, wherein a ratio between the first physiological high frequency exposure value and the second physiological high frequency exposure values is optimized.

4. The method as claimed in claim 1, wherein carrying out the predetermined function comprises detecting magnetic resonance detection signals, pre-processing the magnetic resonance detection signals, transmitting magnetic resonance transmission signals, based on the magnetic resonance detection signals, to an evaluating device, or a combination thereof.

5. The method as claimed in claim 1, wherein determining the energy requirement comprises determining a transfer energy requirement value that indicates an energy required by the local coil system in order to transmit magnetic resonance transmission signals, based on magnetic resonance transmission signals, with a local coil transmission device to the evaluating device, determining a pre-processing energy requirement value that indicates an energy required by the local coil system to evaluate, prepare, or evaluate and prepare magnetic resonance detection signals, or a combination thereof.

6. The method as claimed in claim 1, wherein determining the energy requirement value comprises determining and taking into account information concerning energy stored in an energy store of the local coil system, pulse sequences to be emitted, patient-specific data, a type of examination, an outgoing power and an incoming power of an antenna for transmission of magnetic resonance excitation signals, an outgoing power and an incoming power to an energy supply antenna, or a combination thereof.

7. The method as claimed in claim 1, further comprising switching off at least one energy transfer device during a time period, during which no magnetic resonance signals are to be received.

8. The method as claimed in claim 1, further comprising creating a spatially inhomogeneous energy distribution at least temporarily for energy supply to the local coil system.

9. The method as claimed in claim 2, wherein carrying out the predetermined function comprises detecting magnetic resonance detection signals, pre-processing the magnetic resonance detection signals, transmitting magnetic resonance transmission signals, based on the magnetic resonance detection signals, to an evaluating device, or a combination thereof.

10. The method as claimed in claim 3, wherein carrying out the predetermined function comprises detecting magnetic resonance detection signals, pre-processing the magnetic resonance detection signals, transmitting magnetic resonance transmission signals, based on the magnetic resonance detection signals, to an evaluating device, or a combination thereof.

11. The method as claimed in claim 3, wherein determining the energy requirement comprises determining a transfer energy requirement value that indicates an energy required by the local coil system in order to transmit magnetic resonance transmission signals, based on magnetic resonance transmission signals, with a local coil transmission device to the evaluating device, determining a pre-processing energy requirement value that indicates an energy required by the local coil system to evaluate, prepare, or evaluate and prepare magnetic resonance detection signals, or a combination thereof.

12. The method as claimed in claim 4, wherein determining the energy requirement comprises determining a transfer energy requirement value that indicates an energy required by the local coil system in order to transmit magnetic resonance transmission signals, based on magnetic resonance transmission signals, with a local coil transmission device to the evaluating device, determining a pre-processing energy requirement value that indicates an energy required by the local coil system to evaluate, prepare, or evaluate and prepare magnetic resonance detection signals, or a combination thereof.

13. The method as claimed in claim 2, wherein determining the energy requirement value comprises determining and taking into account information concerning energy stored in an energy store of the local coil system, pulse sequences to be emitted, patient-specific data, a type of examination, an outgoing power and an incoming power to/from an antenna for transmission of magnetic resonance excitation signals, an outgoing power and an incoming power to an energy supply antenna, or a combination thereof.

14. The method as claimed in claim 2, further comprising switching off at least one energy transfer device during a time period, during which no magnetic resonance signals are to be received.

15. The method as claimed in claim 2, further comprising deliberately creating a spatially inhomogeneous energy distribution at least temporarily for energy supply to the local coil system.

16. A local coil energy supply arrangement for a local coil system, the local coil energy supply arrangement comprising:
an energy requirement determination device configured to repeatedly determine a current energy requirement value representing a minimum energy level to be fed to the local coil system for the local coil system to perform a predetermined function over a predetermined time period; and
an energy transfer device operable to wirelessly supply the local coil system with energy for operation of the local coil system, wherein an energy output from the energy transfer device is adaptively controlled depending on the respective determined current energy requirement value.

17. The local coil energy supply arrangement as claimed in claim 16, further comprising an exposure determination device configured to determine a first physiological high frequency exposure value for a patient, the first physiological high frequency exposure value being caused by the wireless supply of the energy to the local coil system, and to determine a second physiological high frequency exposure value being a maximum causable by the imaging, so that a maximum permitted physiological high frequency exposure of the patient is not exceeded.

18. The local coil energy supply arrangement as claimed in claim 16, further comprising:
an energy store monitoring device configured to monitor an energy store and to generate an energy requirement signal that represents an energy status of the energy store; and
a requirement signal detection device configured to receive the energy requirement signal.

19. A local coil system comprising:
a local coil configured to receive magnetic resonance detection signals;
a local coil transmission device configured to transmit magnetic resonance transmission signals wirelessly;
an energy receiving device configured to receive energy wirelessly;
an energy requirement determination device configured to repeatedly determine whether the local coil system requires a supply of energy to carry out each predetermined function over each predetermined time period; and
a requirement signal transmission device configured to transmit an energy requirement signal that indicates the local coil system requires the respective supply of energy.

20. A magnetic resonance system comprising:
a local coil energy supply arrangement, a local coil system, or the local coil energy supply arrangement and the local coil system,
wherein the local coil energy supply arrangement comprises:
an energy requirement determination device configured to repeatedly determine a current energy requirement value representing a minimum energy level to be fed to the local coil system for the local coil system to perform a predetermined function over a predetermined time period; and
an energy transfer device operable to wirelessly supply the local coil system with energy for operation of the local coil system, wherein an energy output from the energy transfer device is adaptively controlled depending on the respective determined current energy requirement value, and
wherein the local coil system comprises:
a local coil configured to receive magnetic resonance detection signals;
a local coil transmission device configured to transmit magnetic resonance transmission signals wirelessly;
an energy receiving device configured to receive energy wirelessly;
an energy requirement determination device configured to repeatedly determine whether the local coil system requires a supply of energy to carry out each predetermined function over each predetermined time period; and
a requirement signal transmission device configured to transmit an energy requirement signal that indicates the local coil system requires the respective supply of energy.

* * * * *